(12) United States Patent
Richter et al.

(10) Patent No.: US 11,680,919 B2
(45) Date of Patent: Jun. 20, 2023

(54) SYSTEM FOR INTERACTING WITH POLYISOPRENE BASED PRODUCTS TO ENHANCE SENSING FEATURES

(71) Applicants: Wolfgang Richter, Vancouver (CA); Faranak Zadeh, Vancouver (CA)

(72) Inventors: Wolfgang Richter, Vancouver (CA); Faranak Zadeh, Vancouver (CA)

(73) Assignee: EPIC SEMICONDUCTORS INC, Columbia (CA)

( * ) Notice: Subject to any disclaimer, the term of this patent is extended or adjusted under 35 U.S.C. 154(b) by 78 days.

(21) Appl. No.: 17/511,025

(22) Filed: Oct. 26, 2021

(65) Prior Publication Data
US 2022/0128499 A1 Apr. 28, 2022

Related U.S. Application Data

(60) Provisional application No. 63/106,257, filed on Oct. 27, 2020.

(51) Int. Cl.
*G01N 27/00* (2006.01)
*H02J 50/00* (2016.01)

(52) U.S. Cl.
CPC ............ *G01N 27/00* (2013.01); *H02J 50/001* (2020.01)

(58) Field of Classification Search
CPC ...... G01N 22/02; G01N 27/00; G01N 33/445; H02J 50/001
See application file for complete search history.

(56) References Cited

U.S. PATENT DOCUMENTS

| | | | | |
|---|---|---|---|---|
| 5,999,004 A | * | 12/1999 | Okawa | G01N 33/445 324/717 |
| 2016/0248481 A1 | * | 8/2016 | Richter | H02J 50/001 |
| 2020/0083010 A1 | * | 3/2020 | Khlat | H04B 1/006 |

* cited by examiner

*Primary Examiner* — Alvaro E Fortich
*Assistant Examiner* — Adam S Clarke (57) ABSTRACT

Disclosed is a system for interacting with polyisoprene based products to enhance sensing features. The system includes a hub unit and one or more electronic circuitries operably configured with the polyisoprene based product. The hub unit includes a controller for contactless powering and communicating data with the polyisoprene based product, a generator for generating a frequency, a resonator for increasing voltage level of the frequency, a first electrode for emitting the alternating electric field, a second electrode for receiving the alternating electric field from the polyisoprene based product, an analog digital converter connected to the second electrode to digitize information received from the polyisoprene based product under the influence of the alternating electric field. The one or more electronic circuitries senses the condition of the polyisoprene based product and communicates further to the hub unit for processing and communicating processed information over a communication network.

11 Claims, 4 Drawing Sheets

SYSTEM FOR INTERACTING WITH POLYISOPRENE BASED PRODUCTS TO ENHANCE SENSING FEATURES

CROSS-REFERENCE TO RELATED APPLICATION

This application claims the benefit of U.S. Provisional application No. 63/106,257, filed Oct. 27, 2020, which is incorporated by reference in its entirety herein.

BACKGROUND OF THE INVENTION

1. Field of the Invention

The present invention generally relates to smart rubber, and more particularly relates to a system for interacting with polyisoprene based products to enhance sensing features.

2. Description of Related Art

Natural and synthetic polymers are widely used in many aspects of today's technology. Rubber is a natural product, available in many forms and functions. They are often used in items and products like tires, hoses, washers, seals, etc. because of their ruggedness and elasticity. The art knows pressure sensitive resistors (FSR) made from polymers; also, polymers are the base carrier for flexible or printed electronics.

Experiments have shown that polymer tapes store electrical charges as information. Polymers also protect embedded electronics circuitry from environmental physical forces or chemical reactions. Various sensors have been attached to the products to sense characteristics of the rubber product and of surroundings.

As the molecular structure of the polymer reflects mechanical and chemical influence or interaction with at least one of but not limited to environment, objects, users, machines, and products (e.g. as changes in electrical impedance and/or resonance) it is possible to monitor such forces with the help of alternating electric fields which are contactless provided (e.g. by an oscillator/electrode combination) over a distance.

Therefore, instead of attaching sensors to a rubber (polymer) item, there is a need to of a system that uses the rubber's (polymer's) inherent features as sensors, as well as its surface as an electrode that conducts electrical energy and information by using its electrons and propagating electrical charges in combination with electronic circuits embedded in/or in reach of the product. Further, the system should not disturb the intended functionality of the rubber (polymer) item.

Further, the system should use natural or synthetic polymers as a key element of harvesting and storing electrical energy or provide additional sensing features to widely enhance their use and turn them from passive into (electro) active items in multiple sensing applications.

SUMMARY OF THE INVENTION

In accordance with teachings of the present invention, a system for interacting with a polyisoprene based product is provided.

An object of the present invention is to provide a system with a hub unit and one or more electronic circuitries capacitively coupled to the hub unit. The hub unit includes a controller, a generator, a resonator, a first electrode, a second electrode, and an analog digital converter. The hub unit communicates modulated data via an alternating electric field with the polyisoprene based product, further digitizes and processes information received from the electronic circuitry.

The electronic circuitry includes an energy harvester, a first logic circuit, a second logic circuit, an analytical unit, and a modulator. The energy harvester creates electrical (DC) energy and synchronous clock signals from the influence of the alternating electric field. The first logic circuit is powered and clocked by the energy harvester to sense changes at a first position on the polyisoprene based product under the influence of the alternating electric field.

The second logic circuit is powered and clocked by the energy harvester to sense changes at a second position on the polyisoprene based under the influence of the alternating electric field. The analytical unit is powered and clocked by the energy harvester for measuring the sensing difference between the first logic circuit and the second logic circuit for calculating a digital value.

The modulator powered by the energy harvester modulates the digital value into the alternating electric field. The modulator communicates the digital value to the controller via the alternating electric field, wherein the controller processes the digital value.

Another objective of the present invention is to position the polyisoprene based product between the first electrode and the second electrode. Further, the analytical unit analyzes the structure and the consistency of the material of the polyisoprene based product.

Another objective of the present invention is to provide the hub unit with a rectifier for creating positive charges from the frequency, a buffer for storing the positive charge against earth's ground, an electronic switch for releasing the positive charges, a control unit for controlling operation of the electronic switch, and a needle electrode configured for emitting the positive charges and for attracting electrons present in the molecular structure of the polyisoprene based product, wherein the electrons are summoned perpendicular to the needle electrode to create a negative zone in the polyisoprene based product to alter structures of the polyisoprene based product.

Another objective of the present invention is to provide the system, wherein the controller loads permanent or temporary electrical charges in the polyisoprene based product. Further, the alternating electrical field changes electrical properties of the polyisoprene based product.

Another objective of the present invention is to provide the system with one or more compounds equipped with the polyisoprene based product to establish a sensing patch. Further, the electronic circuitry senses wear, damage, and imperfections of the polyisoprene based product. Further, the polyisoprene based product floats electrically as a capacitive coupling to the electrical ground of at least one of the earth, a machine, a conductive item, liquids, gases, user, etc.

Another objective of the present invention is to provide the system wherein the digitized value contains changes in the electrical impedance of the polyisoprene based product, wherein the controller processes the digitized value to assess the condition of the polyisoprene based product.

For a better understanding of the present disclosure, together with other and further aspects thereof, reference is made to the following description, taken in conjunction with the accompanying drawings. The scope of the disclosure is set forth in the appended claims, which set forth in detail certain illustrative embodiments. These embodiments are

DETAILED DESCRIPTION OF DRAWINGS

It is to be understood that the embodiments described herein are merely exemplary of the invention, which can be embodied in various forms. Therefore, specific structural and functional details disclosed in relation to the exemplary embodiments described herein are not to be interpreted as limiting, but merely as a representative basis for teaching one skilled in the art to variously employ the present invention in virtually any appropriate form, and it will be apparent to those skilled in the art that the present invention may be practiced without these specific details. Further, the terms and phrases used herein are not intended to be limiting but rather to provide an understandable description of the invention.

The present inventions are now described in detail with reference to the drawings. In the drawings, each element with a reference number is similar to other elements with the same reference number independent of any letter designation following the reference number. In the text, a reference number with a specific letter designation following the reference number refers to the specific element with the number and letter designation and a reference number without a specific letter designation refers to all elements with the same reference number independent of any letter designation following the reference number in the drawings.

It should be appreciated that many of the elements discussed in this specification may be implemented in a hardware circuit(s), a controller/processor executing software code or instructions which are encoded within computer-readable media accessible to the processor, or a combination of a hardware circuit(s) and a processor or control block of an integrated circuit executing machine-readable code encoded within a computer-readable media. As such, the term circuit, module, server, application, or other equivalent description of an element as used throughout this specification is, unless otherwise indicated, intended to encompass a hardware circuit (whether discrete elements or an integrated circuit block), a controller or control block executing code encoded in a computer-readable media, or a combination of a hardware circuit(s) and a processor and/or controller executing such code.

Figure 1:
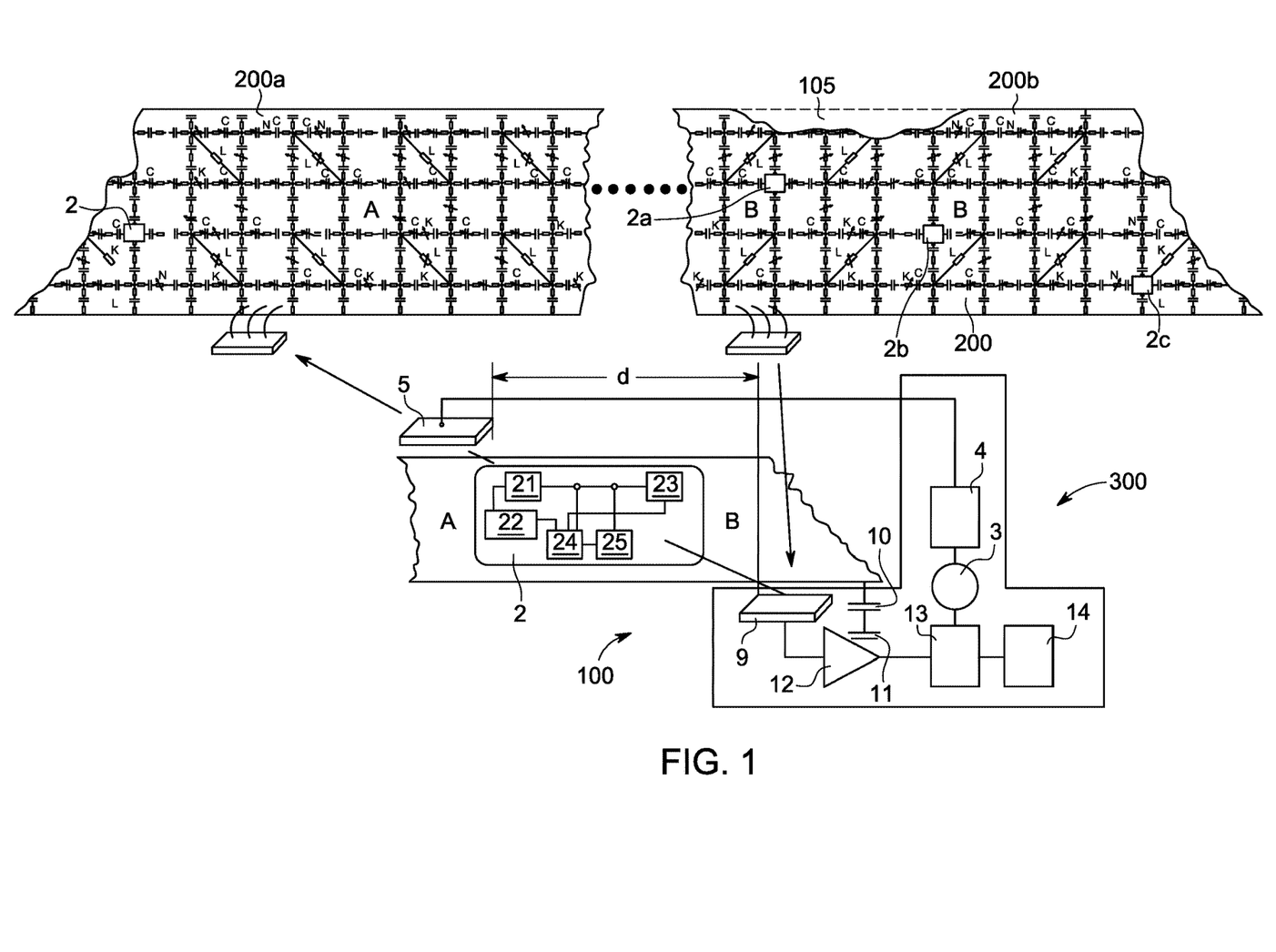
FIG. 1 illustrates a schematic diagram showing a detailed principle of a system interacting with a polyisoprene based product.

FIG. 1 illustrates a schematic diagram showing a detailed principle of the system 100. The system 100 interacts with polyisoprene based products 200 to enhance sensing features. The system 100 includes one or more electronic circuitries 2 (such as 2a, 2b,2c) configured in the polyisoprene based products 200 and a hub unit 300 that capacitively couples with the electronic circuitry 2.

Example of polyisoprene based products 200 include but not limited to a tyre or tire, synthetic rubber, pipes, a seal, a gasket, a washer, a part of machine, a sole of a shoe, a string, combined with fabric, a damper, an air spring, a part of package, a tube, a hose, a conveyor belt, and a medical product etc. The polyisoprene based product 200 hereinafter is mentioned in the specification as a rubber 200, polymer 200, product 200 etc.

The hub unit 300 includes a controller 13, a generator 3, a resonator 4, a first electrode 5, a second electrode 9, and an analog digital converter 12. The controller 13 contactless powers and communicates data with the polyisoprene based product 200. Example of the controller 13 includes but not limited to a microcontroller, FPGAs, PLC, processors, etc.

The generator 3 generates a frequency (e.g. 100 kHz). The resonator 4 increases the voltage level of the frequency. Examples of the generator 3 include but are not limited to oscillators, PWM, toggled I/O pins, PLL, etc. Examples of the resonator 4 include but not limited to a rectifier, inductor, resonator, cascade, diode bridges, transformer, and level shifter.

The first electrode 5 emits the alternating electric field and the second electrode 9 receives the alternating electric field from the polyisoprene based product 2. In a preferred embodiment of the present invention, the polyisoprene based product 2 is positioned between the first electrode 5 and the second electrode 9.

The analog digital converter 12 is connected to the second electrode 9 to digitize digital values received from the electronic circuitry under the influence of the alternating electric field. Examples of the analog digital converter 12 include but not limited to a SAR, ADCs (e.g. Wilkinson/Delta-Sigma/Slope etc.), pulse interval converter (VPIC), VCOs, PLL, MCUs, SOCs, etc.

The one or more electronic circuitries 2 (such as 2a, 2b, 2c) is/are operably configured with the polyisoprene based product 200 and capacitively couple(s) with the hub unit 300. The electronic circuitry 2 includes an energy harvester 21, a first logic circuit 22, a second logic circuit 23, an analytical unit 24, and a modulator 25.

The energy harvester 21 creates electrical (DC) energy and synchronous clock signals from the influence of the alternating electric field. Examples of the energy harvester 21 include but not limited to a Graetz bridge, AC-DC convertor, MOS switches, charge pumps, etc.

The first logic circuit 22 and the second logic circuit 23 are powered and clocked by the energy harvester 21 to sense changes at a first position CA', and a second position CB', respectively on the polyisoprene based product 200 under the influence of the alternating electric field.

Examples of the first logic circuit 22 and the second logic circuit 23 include but not limited to a differential amplifier, instrumentation amplifier, comparator, or in combination. Examples of the changes sensed in the first logic circuit 22 and the second logic circuit 23 include but not limited to detecting wear and damage imperfections in the polyisoprene based product 2.

The analytical unit 24 is powered and clocked by the energy harvester 21 for measuring the sensing difference between the first logic circuit 22 and the second logic circuit 23 for calculating a digital value. Examples of the analytical unit 24 include but not limited to a differential amplifier, instrumentation amplifier, comparator, in combination with analog digital conversion circuitry like ADC, PWM, IQ, etc.

The modulator 25 is powered by the energy harvester 21 for modulating the digital value into the alternating electric field. Further, the modulator 25 communicates the digital value to the controller 13 via the alternating electric field. The controller 13 processes the digital value. Examples of the modulator 25 include but not limited to a digital gate, mixer, transistor, DAC, I/O port, electronic switch, etc.

In another embodiment of the present invention, the hub unit 300 further includes an interface 14 for communicating digital information received from the controller 13. Examples of the interface 14 include but not limited to a serial, USB, Wi-Fi, Bluetooth, GSM, CDMA, LTE, and any other communication devices.

As shown in FIG. 1, In an exemplary embodiment of the present invention, the polyisoprene based product 200 has zones 200A and 200B, where 200A has a normal consistency and 200B has a damaged zone 105. One or more invention-related circuitries 2 (such as 2a, 2b, 2c) are embedded in the polyisoprene based product 200. The molecular structure of the polyisoprene based product 200 material resembles a passive network of capacitors (C), Resistors® and inductors (L).

The energy harvester 21 creates electrical energy (e.g. from the provided alternating electric field, or forces provided by the polyisoprene based product 200 or the environment) and synchronous clock signals from the influence of the externally provided alternating electric field.

The harvester 21 also buffers the energy as DC to operate the integrated electronic parts. The electronic circuitry 2 gets connected to the passive L-R-C network of the material in different zones A and B of the polyisoprene based product 200 and is surrounded by the molecules of the material.

The first logic circuit 22 and the second logic circuit 23 are sensitive to electrical changes caused by forces or structural changes in the polyisoprene based product 200, which is amplified and filtered from the analytical unit 24, preferably a differential or instrumentation amplifier. Further, the result of these measurements may be data modulated with the modulator 25 that modulates the data into the alternating electric field (AM, FM, IQ, on/off, etc.).

The external generator 3 creates a frequency e.g. 100 kHz connected to the modulator resonator 4 that modulates information into the frequency which emits as an alternating electric field from the electrode 5 and influences the polyisoprene based product 200 at the zone A, as well as the embedded electronic circuitries 2 a, b, c . . . n.

The polyisoprene based product 200 floats electrically against ground seen in zone B as a capacitive coupling 10 to the earth's ground 11 (or couples with a machine, vehicle or device, etc.). This creates a difference in the electric field which occurs between the first logic circuit 22 and the second logic circuit 23 of the embedded electronic circuitry 2 a, b, c . . . n, and may be filtered, processed, and analyzed by the differential analytical unit 24.

Further, the resulting findings may be modulated into the provided alternating electric field with the modulator 25 with means of impedance change, subcarrier, and other known or novel modulation techniques. At a distance D is the second electrode 9 that is also influenced by the alternating electric field and further the second electrode 9 is connected to the analog digital converter 12.

The controller 13 is connected to the analog digital converter 12 and further the interface 14 may connect preferably wirelessly to computers and/or networks. Examples of the wireless connections include but not limited to Wi-Fi, Bluetooth, GSM, 5G, RF transceivers, etc.

It is apparent that any mechanical or chemical influence of the polymer A or B changes the molecular structure and therefore the inherent passive L-R-C network which changes dynamically under the influence and the motion of the product 200. It turns the material of the product 200 into a sensor itself that may store or propagate electrical charges that directly or indirectly allow assessments of the internal structure of the product 200 under physical, chemical or environmental stress or influence.

In another embodiment of the present invention, the embedded electronic 2, 2a, 2c, etc. may contain a unique identifier number or code stored in the modulator 25 and is sent to the controller 13, the unique identifier number is read out from the receiving part (electrodes combination 9-12-13) to not only identify the material, but also its current location and speed, in combination with the environmental influence.

Figure 2:
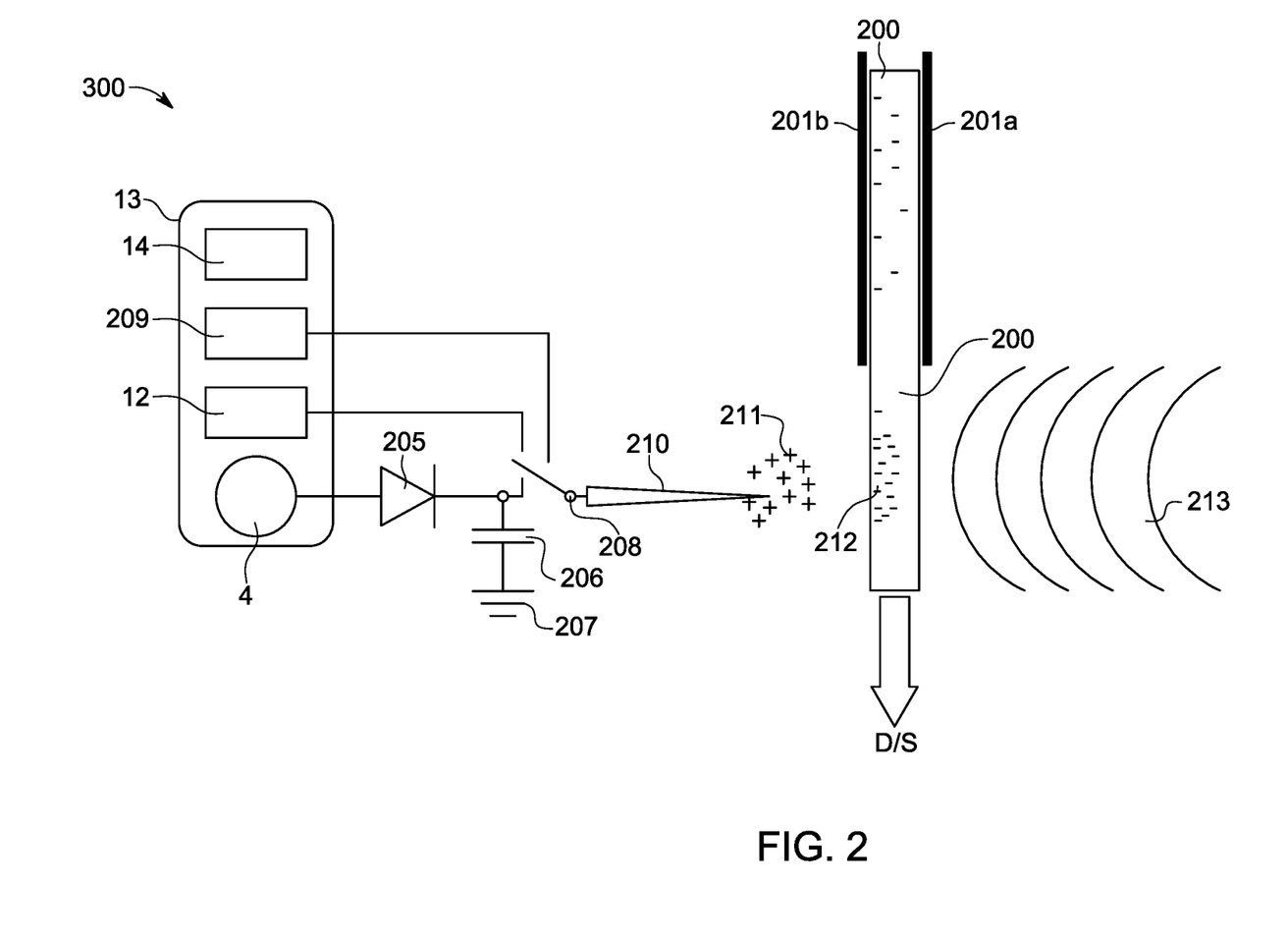
FIG. 2 illustrates a schematic diagram of a system zoning electrical charges into the polyisoprene based product.

FIG. 2 illustrates a schematic diagram of the hub unit 300 zoning electrical charges into the polyisoprene based product 200. Material of the polyisoprene based product 200 may either be a rubber or a similar polymer. The polyisoprene based product 200 passes within an extruder channel 201a, 201b in the direction D with the speed S. The material of the polyisoprene based product 200 is preferably liquefied. The extruder channel 201a, 201b is a machine for pressing the polyisoprene based products such as rubber into molds or forms.

The generator 4 creates a frequency. In another embodiment of the present invention, the hub unit 300 includes a rectifier 205 for creating positive charges from the frequency, a buffer 206 for storing the positive charge against earth's ground 207, an electronic switch 208 that is controlled by a control unit 209 inside the controller 13. Examples of the buffer 206 include but not limited to a capacitor, gold cap, accumulator, rechargeable battery, etc.

Examples of the rectifier 205 include but not limited to diodes, Graetz bridge, phase switches, transmission gates etc. Examples of the electronic switch 208 include but not limited to MOSFET, Opto Coupler, Relays, Transmission gates etc. Examples of the control unit 209 include but not limited to a sequencer, a toggle switch, flip-flop, mono-flop, multi-vibrator, timer, counter etc.

The control unit 209 closes the electronic switch 208 to emit accumulated electric charges over a needle electrode 210 preferably on its tip as a potential electric field 211. Examples of the control unit 209 include but not limited to Logic gates, sequencer, UART, flip flops, registers.

The needle electrode 210 is positioned near the polyisoprene based product 200 and attracts electrons 212 in the material 200, which summon in reach of the tip of the needle 210. The needle electrode 210 may also be used alternatively to the first electrode 5. Due to heat 213, the polyisoprene based product 200 solidifies (cures) and keeps the electrons 212 in the selected area.

The solidified electrons are used to change the electric or dielectric features of the material of polyisoprene based product 200 in this area or to imprint information or alter the physical or chemical or electrical features of the material. For example, a similar procedure may be used in cured polyisoprene based products (such as rubber) 200 by creating temporary zones or "virtual capacitors" of electric charges. These charges or the effect they cause to the material may be read out with the analog digital converter 12 described in detail in conjunction with FIG. 4, of the present invention.

The controller 13 activates the electronic switch 208 over the control unit 209 to receive the electrical charges embedded in the polyisoprene based product 200 over the needle 210. The electronic switch 8 is connected to the analog digital converter 12. The interface 14 inside the controller 13 may send or receive information regarding the features or consistency of the related polyisoprene based product 200.

Further, the controller 13 may be remotely (and preferably wirelessly) powered and operated. The controller 13 may be configured with including but not limited to (rechargeable) batteries, energy harvesters (based on light, magnetic, waves, vibration, temperature, dynamos, etc.), RF or microwaves, etc. As a variation, reverse polarity may be used to create zones in the polymer with less electrons, while alternating polarity may be used to electrically homogenize the polyisoprene based product 200.

Figure 3:
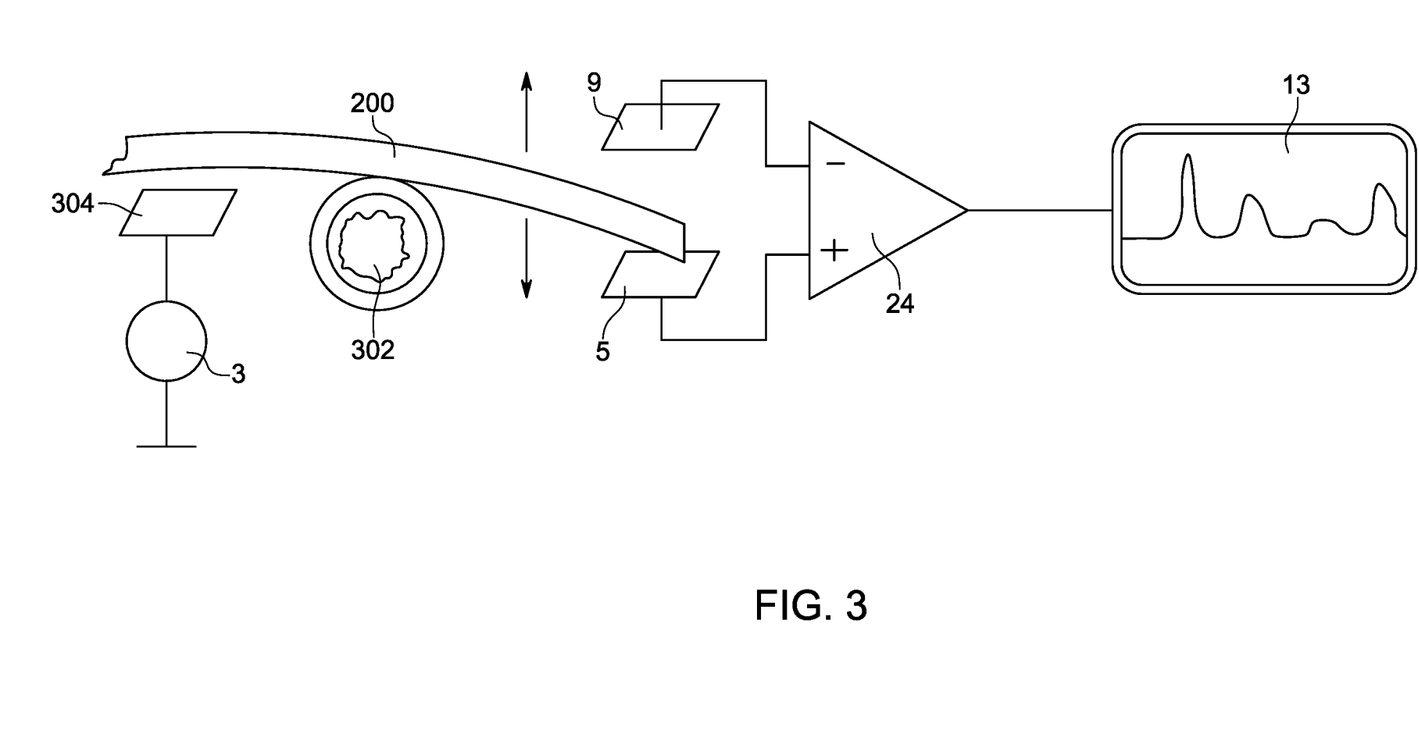
FIG. 3 illustrates a schematic diagram showing a moving polyisoprene based product in an exemplary embodiment of the present invention.

FIG. 3 illustrates a schematic diagram showing a moving polyisoprene based product 200 (such as a tire or a conveyor belt), in an exemplary embodiment of the present invention. The polyisoprene based product 200 is transported, centered or configured around a ball bearing 302 which may have damage, friction, or other malfunctions.

The generator 3 provides an alternating electric field e.g. 100 kHz which emits over an electrode 304 in reach of the polyisoprene based product 200 which gets influenced by the alternating electric field. Examples of the generator 3 include but not limited to a digital or analog oscillator, PWM, multi-vibrator, PLL, etc.

The alternating electric field either propagates through the polyisoprene based product 200 or puts electrical charges in passing zones of the polyisoprene based product 200. The imbalance of the ball bearing 302 causes the polyisoprene based product 200 to vibrate and/or slow down.

The impedance passes through the first electrode 5 and/or the second electrode 9, to be analyzed by the connected analytical unit 24 (such as differential or instrumentation amplifier (INA)) on receiving the charges modulated with the vibration. Common mode rejection suppresses the alternating electric field while the modulation may be amplified and analyzed in the controller 13, which is able to classify the defect of the ball bearing 302 e.g. with classification methods such as at least one of machine learning, pattern recognition, Artificial Intelligence, or mathematical methods (FFT, DFT, wavelets, spectrum analytics, etc.).

As shown, the system works preferably contactless and non-destructive to the moving polyisoprene based product 200. It may be used for security features, improve safety requirements or engage maintenance prediction. It is also possible that the invention may be used as a tool.

Further the generator 3 and/or analyzer/controller 13 may be remotely (and preferably wirelessly) powered and operated. Examples of powering include but not limited to (rechargeable) batteries, energy harvesters (based on light, magnetic, waves, vibration, temperature, dynamos, etc.), RF or microwaves, etc.

Figure 4:
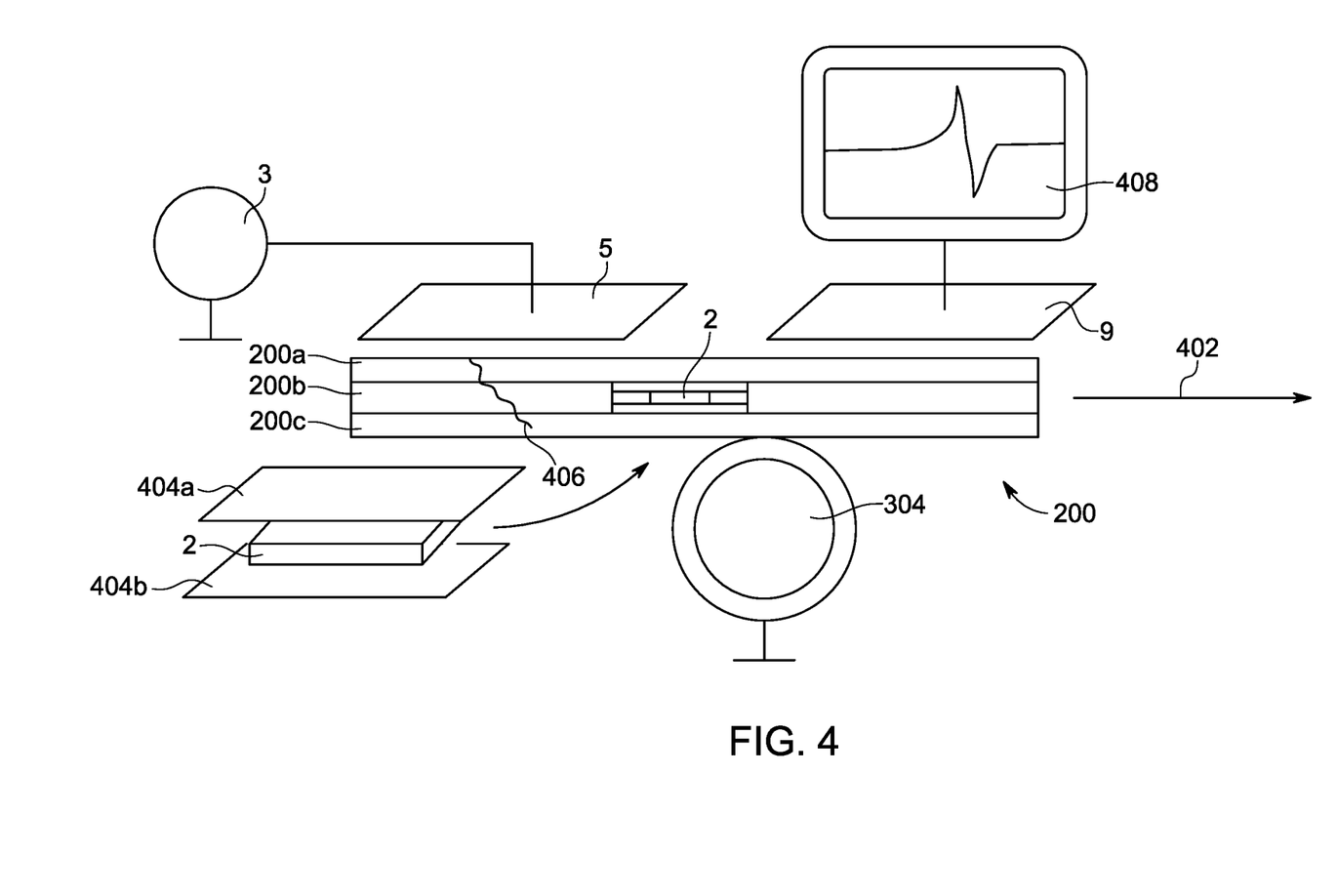
FIG. 4 illustrates a schematic diagram of the system wherein an electronic circuitry (IC) is embedded in a layered polymer/rubber.

FIG. 4 illustrates a schematic diagram of the system 100 wherein the electronic circuitry 2 is embedded in a polyisoprene based product 200 in an exemplary embodiment of the present invention. The polyisoprene based product 200 is shown in multiple layers such as 200a, 200b, 200c.

The generator 3 creates a frequency which emits as an alternating electric field from the electrode 5 and influences the material of polyisoprene based product 200, which may be moving in a direction 402 with a certain speed over or centered on a ball bearing 304. The embedded electronic circuitry 2 consists of sub-circuits (described in detail in conjunction with FIG. 1 to FIG. 3) and is sandwiched between conductive electrodes 404a, 404b.

The polyisoprene based product 200 may have at least one hidden damage 406 which may cause failure during the operation. The alternating electric field (not shown) propagates either through the polyisoprene based product 200 or creates temporary charges that influence the implanted electronic circuitry 2.

Further, the electric field is received from the second electrode 9 which is connected to the analytical unit, hereinafter in the specification is termed as detector 408 which analyzes the structure and consistency of material of the polyisoprene based product 200. The detector 408 also alerts first responders or maintenance personnel or records information regarding the consistency of the moving polymer.

The implanted electronic circuitry 2 is able to check the passive (L,R,C) network caused by the molecular structure inside the polymer and modulates sensing, measurement, or calculation results into the alternating electric field to be received from the second electrode 9 and further processed from the detector 408 which further communicates with the computers or networks via the interface (14, as shown in FIG. 1). Examples of the detector 408 (analytical unit) include but not limited to analog or digital computing, calculators, MCU's, edge A.I., FPGAs, etc.

The layers (200a,b,c) of the polyisoprene based product 200 may also be conductive or dielectric or in-between. The structural damage 406 may be a crack or an imperfection, a gas bubble or a punch hole or a penetrated object e.g. metal splinter, etc., and is detected and communicated from both, the embedded electronic circuitry 2 as well as the connected detector 408 (via the electron entanglement of the capacitive coupling).

In an exemplary embodiment, the related electronic circuitry may be embedded in moving rubber parts like tires or conveyor belts to monitor environmental influence, wear and tear, damage imperfections, etc. A typical example is to measure conditions inside or outside a tire, an air-spring, tube, or hose regarding pressure, flow, temperature, humidity, speed, viscosity, clogging, damages, etc.

Environmental changes may change the material. A tire behaves differently in winter than in summer, abrasion or loss of profile needs to be detected which the invention serves in a preferably way as well as other aspects in regards to assessing the flexibility or elasticity of the material. Additionally, the invention indirectly may measure or assess the surrounding equipment, for example the ball bearings of a tire or a conveyor belt, shock absorbers, loads, vibrations, resonances, etc. A main aspect is that all these measurements may be performed contactless and with no harm to the polymer/rubber.

In another exemplary embodiment of the present invention, compounds may be mixed with the polymer/rubber that are sensitive to (bio-)chemical reactions caused by substances or bacteria. It is therefore possible e.g. to equip the surface of a polymer patch with substances that may cause allergic reactions on a human (users) skin when applied. Examples of the compounds include but not limited to carbon, fibers, glues, conductive or dielectric material, metal, gases, chemical or biological markers, etc.

An allergic reaction is a high molecular activity from a physical point of view that may be measured and communicated through the embedded electronics inside the polymer patch, while the user and the patch are influenced by an alternating electric field provided from the invention-related generator. Further, the received information is processed and propagated as shown in the drawings.

In another embodiment of the present invention, the embedded circuitry and the rubber may be a part of clothes or e.g. the sole of a shoe. The user may carry a controller which propagates the generated alternating electric field over the human skin. It influences the polymer in the shoe's sole and floats against the earth's ground. The embedded electronic circuitry may measure weights, impacts, torque, angles, time of flight, step rate, step width, vital signs, etc.

provided by the user during action (e.g. sport, work, service, etc.) as well as environmental influences.

In another embodiment of the present invention, the system may be used for identification purposes. The embedded electronic circuitry may have a unique identifier number or code, which is also sent to the controller (e.g. by modulating the alternating electric field, or a transmitter) for further processing. This may be helpful concerning products in protection, storing, inventory, sales, use and recycle situations.

The polymer may also be (a part of) the package for a product or item to control its status during production, transportation, storing in a warehouse, presenting in shops or use. Polymers of this kind may also make home appliances and industrial machines safer as they detect the approach and interaction of humans or objects (as changes in the impedance) when in reach of the alternating electric field.

In another embodiment, the polymer or rubber may have the form as a seal ring or washer for lids, valves, rivets or screws (nuts and bolts) to measure forces, actions, and events with the embedded electronic circuitry and further communicate such to networks over the remote controller influenced by its provided alternating electric field. In another embodiment of the invention, the system may sense the elasticity of air- or gas-filled chambers acting as air springs e.g. in vehicles or as dampers for machines.

In another embodiment of the invention the system utilizes the polymer or rubber as elastic strings or rubber bands or other forms of dampers or shock absorbers. Variations of the invention may be sensing mats for object detection and changes in their behavior. The objects may be humans, animals, plants or any object of interest. Those who skilled in the art will envision multiple uses of the system in various polyisoprene based products without deviating from the scope of the present invention.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The invention claimed is:

1. A system for interacting with polyisoprene based products to enhance sensing features, the system comprising:
a hub unit comprising:
a controller for contactless powering and communicating data with the polyisoprene based product;
a generator for generating a frequency;
a resonator for increasing voltage level of the frequency;
a first electrode for emitting the alternating electric field;
a second electrode for receiving the alternating electric field from the polyisoprene based product; and
an analog digital converter connected to the second electrode to digitize digital values received from the electronic circuitry under the influence of the alternating electric field;
one or more electronic circuitries operably configured with the polyisoprene based product and capacitively coupled with the hub unit, wherein each electronic circuitry comprising:
an energy harvester creates electrical energy and synchronous clock signals from the influence of the alternating electric field;
a first logic circuit powered and clocked by the energy harvester to sense changes at a first position on the polyisoprene based product under the influence of the alternating electric field;
a second logic circuit powered and clocked by the energy harvester to sense changes at a second position on the polyisoprene based under the influence of the alternating electric field;
an analytical unit powered and clocked by the energy harvester for measuring the sensing difference between the first logic circuit and the second logic circuit for calculating a digital value; and
a modulator powered by the energy harvester for modulating the digital value into the alternating electric field, further the modulator communicates the digital value to the controller via the alternating electric field,
wherein the controller processes the digital value.

2. The system according to claim 1 wherein the polyisoprene based product is positioned between the first electrode and the second electrode.

3. The system according to claim 1, wherein the analytical unit analyzes structure and consistency of material of the polyisoprene based product.

4. The system according to claim 1, wherein the hub unit further comprising:
a rectifier for creating positive charges from the frequency;
a buffer for storing the positive charges against earth's ground;
an electronic switch for releasing the positive charges;
a control unit for controlling operation of the electronic switch; and
a needle electrode configured in the electronic circuitry for emitting the positive charges and for attracting electrons present in material of the polyisoprene based product, wherein the electrons are summoned perpendicular to the needle electrode to create a negative zone in the polyisoprene based product to alter structures of the polyisoprene based product.

5. The system according to claim 1 wherein the controller loads permanent or temporary electrical charges in the polyisoprene based product.

6. The system according to claim 1 wherein the modulator stores a unique identifier number to identify location and features of the polyisoprene based product, further communicating the unique identifier to the controller.

7. The system according to claim 1 wherein the alternating electrical field changes electrical properties of the polyisoprene based product.

8. The system according to claim 1 further comprises one or more compounds equipped with the polyisoprene based product to establish a sensing patch.

9. The system according to claim 1, wherein the electronic circuitry senses wear and damage imperfections of the polyisoprene based product.

10. The system according to claim 1, wherein the electronic circuitry senses at least one of: manipulation of the polyisoprene based product; physical forces on the polyisoprene based product; and chemical reactions on the polyisoprene based product.

11. The system according to claim 1, wherein the polyisoprene based product floats electrically as a capacitive coupling to an electrical ground.

* * * * *